United States Patent
Pauley et al.

(10) Patent No.: US 12,178,572 B1
(45) Date of Patent: Dec. 31, 2024

(54) BLOOD GLUCOSE SENSING SYSTEM

(71) Applicant: Masimo Corporation, Irvine, CA (US)

(72) Inventors: Kevin Hughes Pauley, Temecula, CA (US); Hoi Wong, Lake Forest, CA (US); Jesse Chen, Foothill Ranch, CA (US); Mathew Paul, Foothill Ranch, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/428,921

(22) Filed: Jan. 31, 2024

Related U.S. Application Data

(60) Division of application No. 16/805,510, filed on Feb. 28, 2020, now abandoned, which is a continuation of application No. 14/302,417, filed on Jun. 11, 2014, now abandoned.

(60) Provisional application No. 61/913,331, filed on Dec. 8, 2013, provisional application No. 61/898,483, filed on Nov. 1, 2013, provisional application No. 61/833,515, filed on Jun. 11, 2013.

(51) Int. Cl.
*A61B 5/145* (2006.01)
*A61B 5/00* (2006.01)
*G16H 50/20* (2018.01)

(52) U.S. Cl.
CPC ........ *A61B 5/14532* (2013.01); *A61B 5/7275* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,377,676 A | 1/1995 | Vari et al. |
| 5,431,170 A | 7/1995 | Mathews |
| 5,436,499 A | 7/1995 | Namavar et al. |
| 5,452,717 A | 9/1995 | Branigan et al. |

(Continued)

OTHER PUBLICATIONS

US 2022/0192529 A1, 06/2022, Al-Ali et al. (withdrawn)

(Continued)

*Primary Examiner* — Manuel A Mendez
(74) *Attorney, Agent, or Firm* — Knobbe, Martens, Olson & Bear, LLP

(57) ABSTRACT

A blood glucose sensing system includes a plurality of physiological sensors. The system can estimate blood glucose based on discrete invasive blood glucose estimates from a blood sample, discrete noninvasive blood glucose estimates derived from optical sensors, and continuously-calculated blood glucose estimates derived from a nonlinear state-space model of glucose and insulin reactions within a human body. The state-space model has user-entered values corresponding to their insulin and meal intake. The user's blood glucose is estimated from a combination of the discrete invasive blood glucose estimates, the discrete noninvasive blood glucose estimates and the continuously-calculated blood glucose estimate.

18 Claims, 11 Drawing Sheets

(56) References Cited

U.S. PATENT DOCUMENTS

| | | | |
|---|---|---|---|
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,590,649 A | 1/1997 | Caro et al. | |
| 5,602,924 A | 2/1997 | Durand et al. | |
| 5,605,152 A * | 2/1997 | Slate | G01N 21/7703 600/316 |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,066,204 A | 5/2000 | Haven | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,280,381 B1 | 8/2001 | Malin et al. | |
| 6,285,896 B1 | 9/2001 | Tobler et al. | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kiani et al. | |
| 6,661,161 B1 | 12/2003 | Lanzo et al. | |
| 6,671,531 B2 | 12/2003 | Al-Ali | |
| 6,675,030 B2 | 1/2004 | Ciurczak et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,738,652 B2 | 5/2004 | Mattu et al. | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,788,965 B2 | 9/2004 | Ruchti et al. | |
| 6,792,300 B1 | 9/2004 | Diab et al. | |
| 6,813,511 B2 | 11/2004 | Diab et al. | |
| 6,816,241 B2 | 11/2004 | Grubisic | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |

(56) References Cited

U.S. PATENT DOCUMENTS

| | | |
|---|---|---|
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,923,763 B1 * | 8/2005 | Kovatchev ............ G16H 20/17 128/920 |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |

(56) References Cited

U.S. PATENT DOCUMENTS

| | | | |
|---|---|---|---|
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |

(56) References Cited

U.S. PATENT DOCUMENTS

| | | |
|---|---|---|
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Kiani |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |

(56) References Cited

U.S. PATENT DOCUMENTS

| | | |
|---|---|---|
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali et al. |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 10,524,706 B2 | 1/2020 | Telfort et al. |
| 10,524,738 B2 | 1/2020 | Olsen |
| 10,531,811 B2 | 1/2020 | Al-Ali et al. |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,548,561 B2 | 2/2020 | Telfort et al. |
| 10,555,678 B2 | 2/2020 | Dalvi et al. |

(56) References Cited

U.S. PATENT DOCUMENTS

| | | |
|---|---|---|
| 10,568,553 B2 | 2/2020 | O'Neil et al. |
| RE47,882 E | 3/2020 | Al-Ali |
| 10,575,779 B2 | 3/2020 | Poeze et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0038080 A1 | 3/2002 | Makarewicz et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0039271 A1 | 2/2004 | Blank et al. |
| 2004/0106163 A1 | 6/2004 | Workman et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0183060 A1 | 7/2008 | Steil et al. |
| 2008/0200783 A9 | 8/2008 | Blank et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |

(56) References Cited

U.S. PATENT DOCUMENTS

| | | |
|---|---|---|
| 2009/0312621 A1* | 12/2009 | Verbitskiy .............. G16H 50/30 600/365 |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |

(56) References Cited

U.S. PATENT DOCUMENTS

| | | |
|---|---|---|
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0256087 A1 | 9/2016 | Doyle, III et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224233 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |

(56) References Cited

U.S. PATENT DOCUMENTS

| | | |
|---|---|---|
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali et al. |
| 2019/0357812 A1 | 11/2019 | Poeze et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali et al. |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000340 A1 | 1/2020 | Wojtczuk et al. |
| 2020/0000415 A1 | 1/2020 | Barker et al. |
| 2020/0015716 A1 | 1/2020 | Poeze et al. |
| 2020/0021930 A1 | 1/2020 | Iswanto et al. |
| 2020/0029867 A1 | 1/2020 | Poeze et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0375549 A1 * | 12/2020 | Wexler .................. G16H 50/20 |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |

(56) References Cited

U.S. PATENT DOCUMENTS

2024/0122486 A1    4/2024   Kiani
2024/0180456 A1    6/2024   Al-Ali

OTHER PUBLICATIONS

US 2024/0016391 A1, 01/2024, Lapotko et al. (withdrawn)
Briegel et al., "A Nonlinear State Space Model for the Blood Glucose Metabolism of a Diabetic", Anwendungsaufsatz, May 2002, pp. 228-236.
Facchinetti et al., "An Online Failure Detection Method of the Glucose Sensor-Insulin Pump System: Improved Overnight Safety of Type-1 Diabetic Subjects", Feb. 2013, IEEE Transactions on Biomedical Engineering, vol. 60, No. 2, pp. 406-416.
Hovorka et al., "Nonlinear Model Predictive Control of Glucose Concentration in Subjects with Type 1 Diabetes", Physiological Measurement, Aug. 2004, vol. 4, pp. 905-920.
Vashist et al., "Non-invasive glucose monitoring technology in diabetes management: A review", 2012, Analytica Chimica Acta, vol. 750, pp. 16-27.
Wang, PhD et al., "Personalized State-space Modeling of Glucose Dynamics for Type 1 Diabetes Using Continuously Monitored Glucose, Insulin Dose, and Meal Intake: An Extended Kalman Filter Approach", 2014, Journal of Diabetes Science and Technology, vol. 8, No. 2, pp. 331-345.

\* cited by examiner

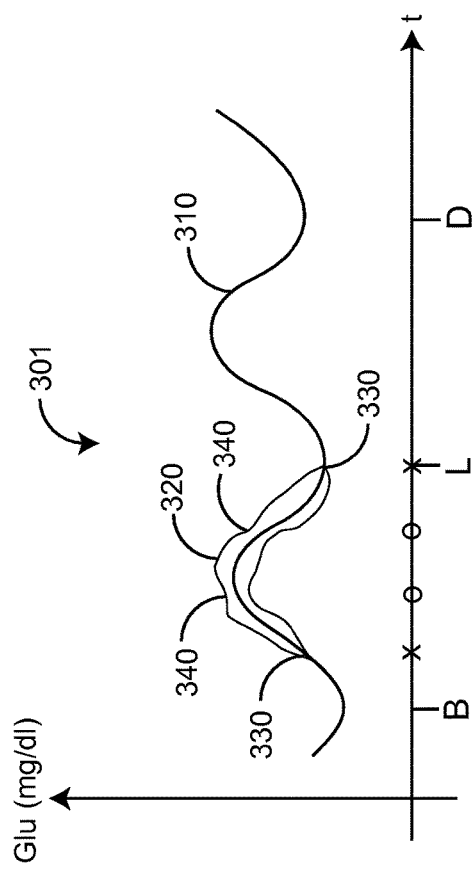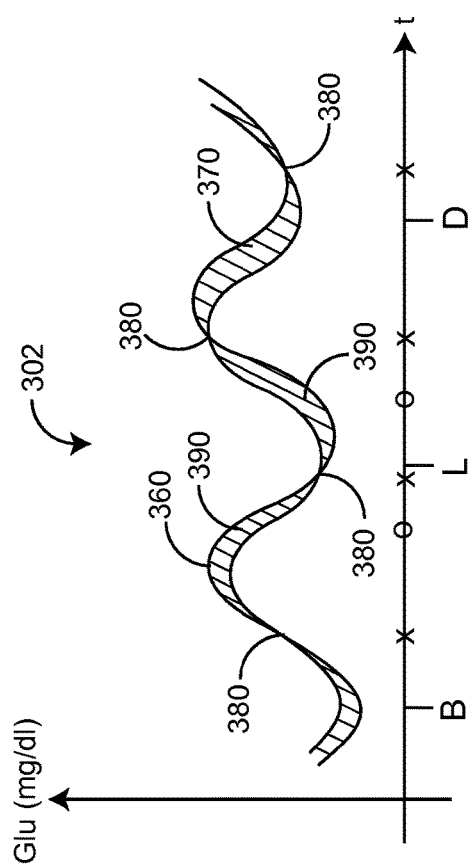

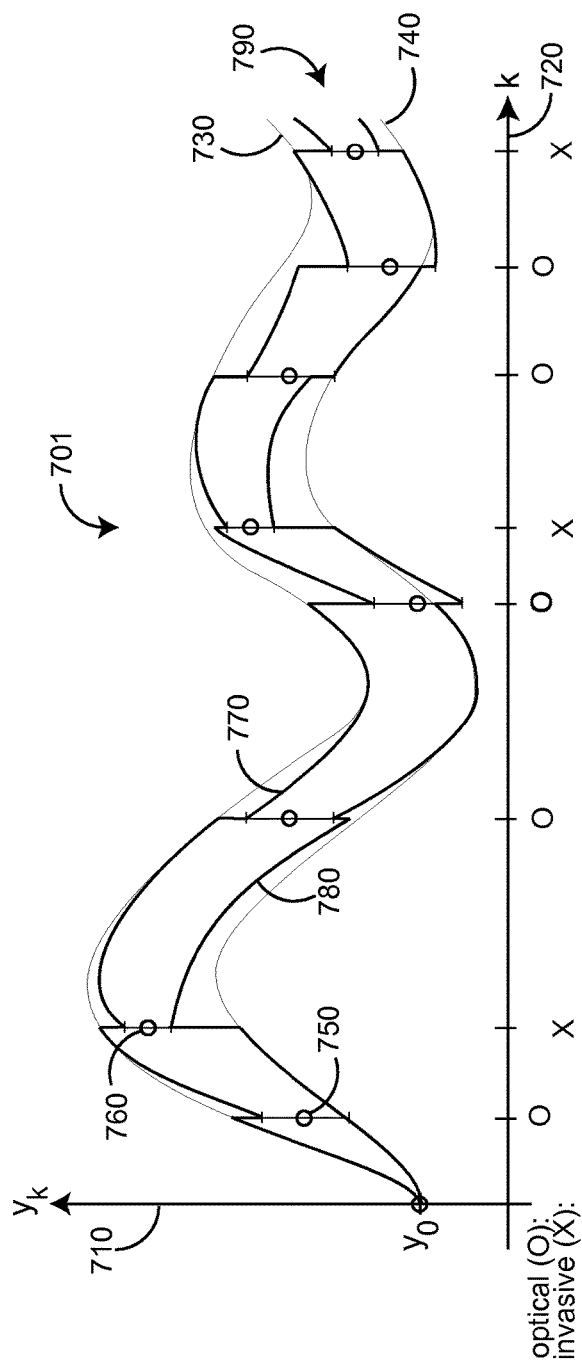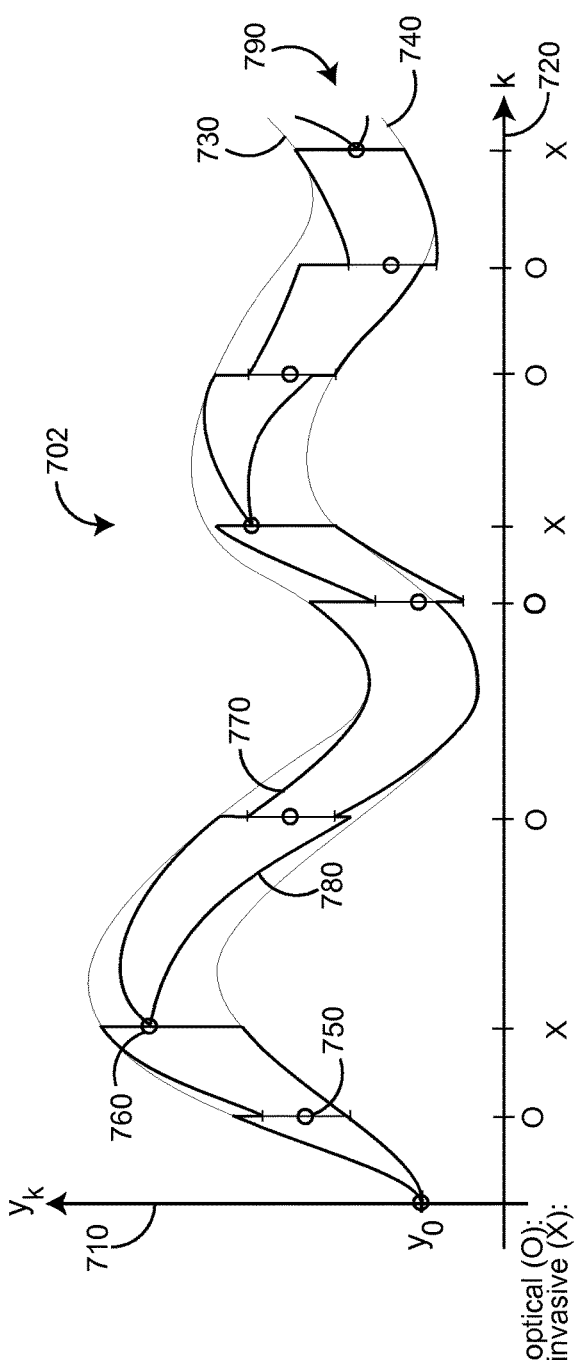

BLOOD GLUCOSE SENSING SYSTEM

PRIORITY CLAIM AND REFERENCE TO RELATED APPLICATIONS

The present application is a divisional of U.S. patent application Ser. No. 16/805,510, filed Feb. 28, 2020, entitled Blood Glucose Estimator, which itself is a continuation of U.S. patent application Ser. No. 14/302,417, filed Jun. 11, 2014, entitled Blood Glucose Estimator, which claims priority benefit under 35 U.S.C. § 119 (e) to U.S. Provisional Patent Application Ser. No. 61/833,515, filed Jun. 11, 2013, titled Blood Glucose Interpolator; U.S. Provisional Patent Application Ser. No. 61/898,483, filed Nov. 1, 2013, titled Glucose Predictor; and U.S. Provisional Patent Application Ser. No. 61/913,331, filed Dec. 8, 2013, titled Blood Glucose Interval Simulator. Each of the above-referenced provisional applications is hereby incorporated in its entirety by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a photoplethysmograph signal responsive to the emitted light after attenuation by pulsatile blood flow within the tissue site. The cable transmits the detector signal to the monitor, which processes the signal to provide a numerical readout of oxygen saturation ($SpO_2$) and pulse rate, along with an audible pulse indication of the person's pulse. The photoplethysmograph waveform may also be displayed.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, all assigned to Masimo Corporation ("Masimo") of Irvine, California and all hereby incorporated in their entireties by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are all also assigned to Masimo and are also all hereby incorporated in their entireties by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, which are all assigned to Cercacor Laboratories, Inc., Irvine, CA (Cercacor) and all hereby incorporated in their entireties by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and herby incorporated in its entirety by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE INVENTION

FIG. 1 generally illustrates a blood glucose measurement system 100 that advantageously combines relatively frequent noninvasive measurements of blood glucose interspersed with relatively infrequent invasive measurements of blood glucose so as to manage individual blood glucose levels. The blood glucose measurement system 100 has a blood glucose monitor 110, an optical sensor 120, a sensor cable 130 electrically and mechanically interconnecting the monitor 110 and sensor 120 and a monitor-integrated test strip reader that accepts test strips 150 via a test strip slot 140. In particular, the blood glucose measurement system 100 individually calibrates the noninvasive optical sensor 120 measurements with intermittent test strip measurements to provide the accuracy of individualized glucose test strip measurements at a much-reduced frequency of blood draws. Reduced blood draws are a substantial aid to persons who require frequent monitoring of blood glucose levels to manage diabetes and related diseases. In an embodiment, the monitor 110 has a handheld housing including an integrated touch screen 160 defining one or more input keys and providing a display of blood glucose levels among other features. An optical sensor is described in detail with respect to U.S. patent Ser. No. 13/646,659 titled Noninvasive Blood Analysis System, filed Oct. 5, 2012, assigned to Cercacor and hereby incorporated in its entirety by reference herein. A blood glucose monitor is described in detail with respect to U.S. patent Ser. No. 13/308,461 titled Handheld Processing Device Including Medical Applications for Minimally and Noninvasive Glucose Measurements, filed Nov. 30, 2011, assigned to Cercacor and hereby incorporated in its entirety by reference herein. A blood glucose monitor and sensor are described in U.S. Ser. No. 13/473,477 titled Personal Health Device, filed May 16, 2012, assigned to Cercacor and hereby incorporated in its entirety by reference herein.

FIGS. 2A-B illustrate a glucose monitor 200 having a optical sensor 210 input for generating noninvasive spot check estimates of blood glucose 252 and a test strip 220 input for generating invasive spot check estimates of blood glucose 252. As shown in FIG. 2A, a signal processor 230 analyzes the optical sensor 210 signals so as to generate the noninvasive spot check estimates. A strip reader 240 analyzes blood draw test strips 220 so as to generate the invasive spot check estimates. An output processor 250 integrates the noninvasive and invasive spot checks into a single blood glucose estimate $\widehat{GLu}$ output 252. As shown in FIG. 2B, error measurements $\varepsilon_i$, $\varepsilon_n$ are incorporated into the blood glucose spot check measurements. The invasive 260 glucose measurement error is substantially less than the noninvasive 270 glucose measurement error $\varepsilon_n$.

One aspect of a blood glucose estimator has discrete invasive blood glucose values derived from a blood sample, discrete noninvasive blood glucose values derived from optical sensor data and modeled blood glucose values derived from a nonlinear state-space model of glucose and insulin reactions within a human body. The state-space model has user-entered values corresponding to insulin and meal intake. A glucose estimate is derived from a combination of the discrete invasive blood glucose values, the discrete noninvasive blood glucose values and the modeled blood glucose values.

In various embodiment, the modeled blood glucose values provide an interval of blood glucose values based upon simulation of extreme values of derivates of the state variables in the state-space model. The interval of blood glucose values collapses to an error $\varepsilon_i$ at the discrete invasive blood glucose values. The interval of blood glucose values collapses to an error $\varepsilon_n$ at the discrete noninvasive blood glucose values. The parameters of the state-space model are dynamically optimized to minimize an error between calculated values of blood glucose and measured values of blood glucose. The values corresponding to insulin and meal intake are derived from weighted optical sensor data ratios. The weighted optical sensor data ratios are dynamically optimized to minimize an error between calculated values of blood glucose and measured values of blood glucose.

BRIEF DESCRIPTION OF THE DRAWINGS

FIGS. 3A-B are graphical display embodiments of a glucose trend and corresponding glucose trend intervals versus time;

FIGS. 7A-B are graphs of blood glucose interval estimates incorporating and responsive to both invasive and noninvasive (optical sensor) blood glucose spot checks;

DETAILED DESCRIPTION OF THE PREFERRED EMBODIMENT

Figure 1:
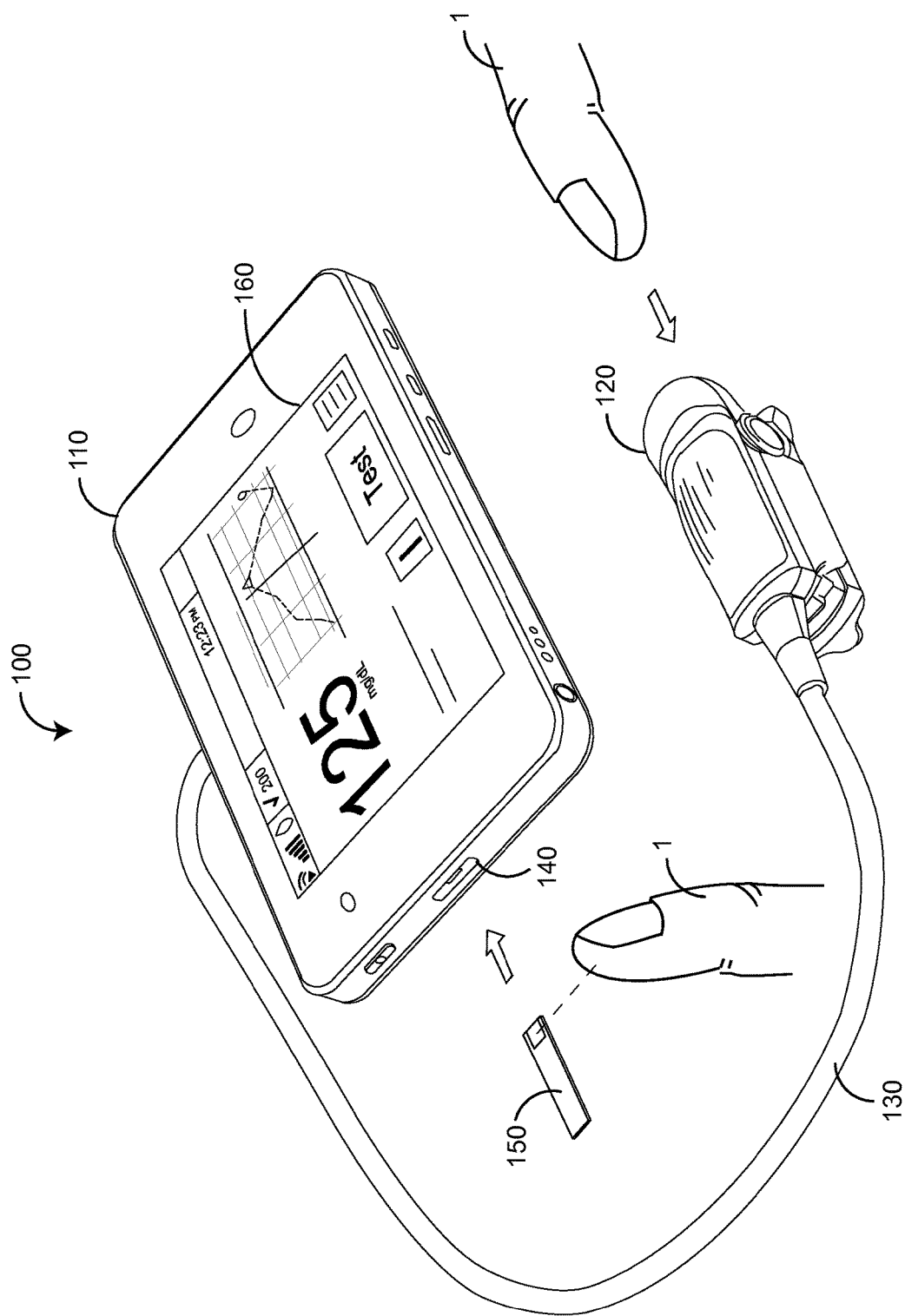
FIG. 1 is an illustration of a blood glucose measurement system.
Figure 2A:
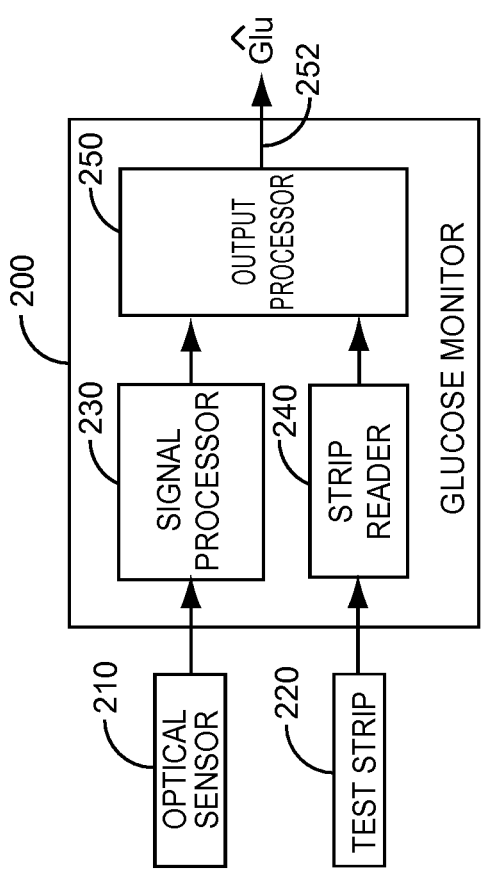
FIGS. 2A-B are a block diagram of a glucose monitor and a corresponding graph of discrete glucose estimates versus time.
Figure 2B:
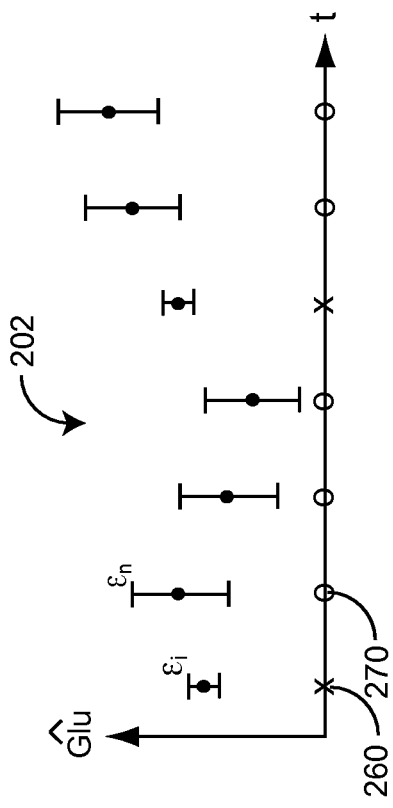

FIGS. 3A-B graphically illustrate interpolation between the discrete invasive (260 FIG. 2B) and noninvasive (270 FIG. 2B) measures described with respect to FIGS. 2A-B, above. FIG. 3A illustrates a glucose monitor output (252 FIG. 2A) embodiment 301 displaying a glucose trend 310 versus time. The trend 310 reflects, say, the rise and fall of glucose levels after breakfast (B), lunch (L) and dinner (D). An envelope 320 is generated to show trend accuracy. The envelope 320 generally coincides to the trend line 310 at invasive glucose spot checks (x) 330 and is reduced in breadth at noninvasive (optical) glucose spot checks (o) 340, reflecting the relative accuracy of these invasive and noninvasive measurements. FIG. 3B illustrates another glucose monitor output (252 FIG. 2A) embodiment 302 where the trend 360 has various areas 370, 380, 390 that reflect measurement accuracy. Invasive spot checks are reflected at trend nodes 380. Noninvasive spot checks are reflected at reduced size trend areas 390. Other areas 370 reflect an interpolation between glucose spot checks and modeled (calculated) glucose values so as to generate an estimated blood glucose output, as described with respect to FIG. 4, below. Interpolation between invasive and noninvasive glucose spot checks is described in detail with respect to interval simulation embodiments, below.

Figure 4:
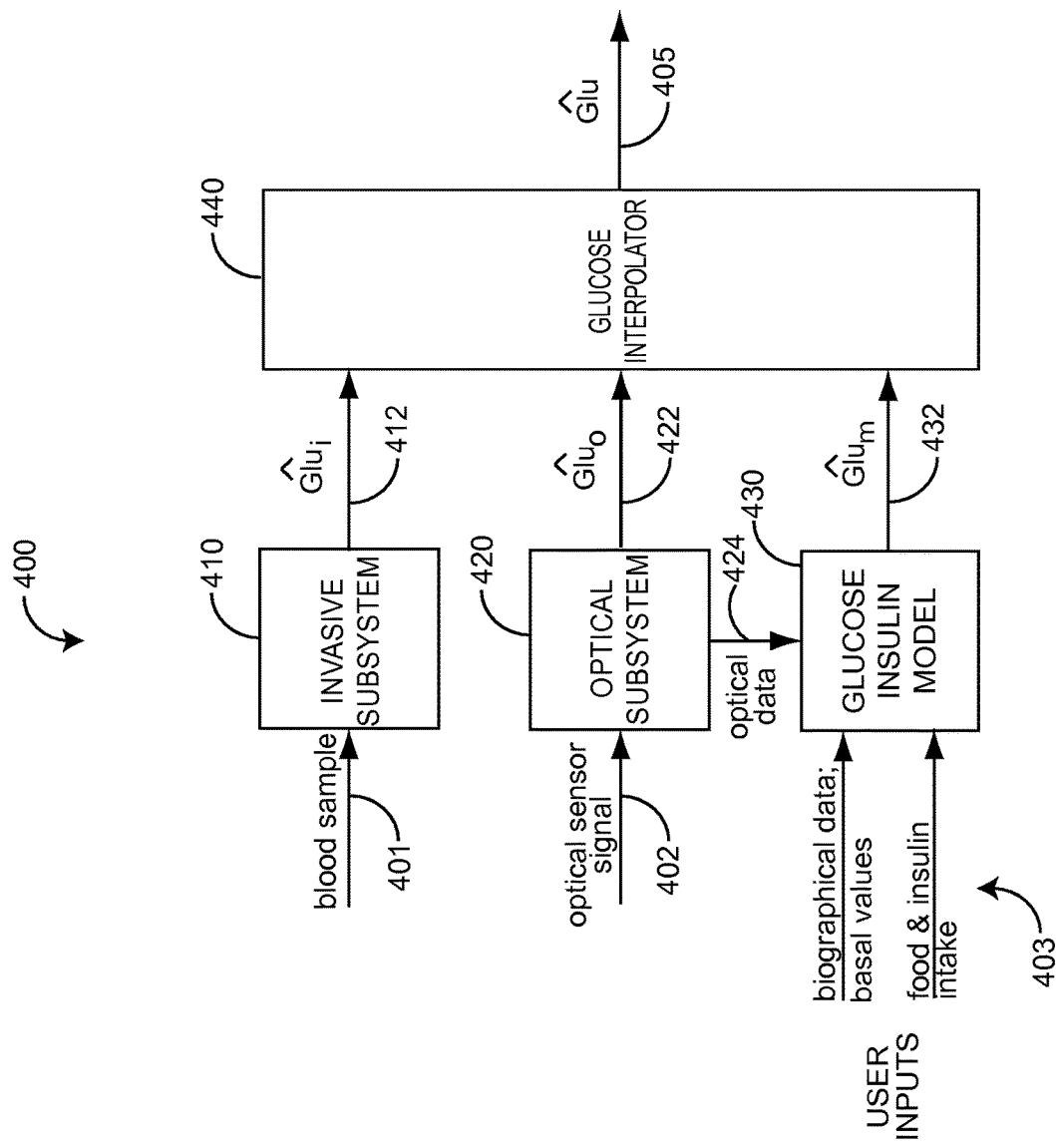
FIG. 4 is a general block diagram of a blood glucose estimator.

FIG. 4 generally illustrates a blood glucose estimator 400 having an invasive subsystem 410 for generating relatively accurate spot checks 412 of blood glucose utilizing a test strip and test strip reader (not shown). In particular, the test strip collects a blood sample 401 and a test strip reader reads the test strip to yield an invasive measure of blood glucose $\widehat{GLu}_i$ 412. The glucose estimator 400 also has an optical subsystem 420 for generating less accurate, but painless, spot checks 422 of blood glucose using an optical sensor 402. In particular, the optical sensor 402 transmits light into a tissue site and detects the light after tissue attenuation to yield a noninvasive (optical) measure of blood glucose $\widehat{GLu}_o$ 422. These spot checks 412, 422 provide discrete glucose inputs to a glucose interpolator 440, which generates a blood glucose estimate $\widehat{GLu}$ 405 based upon $\widehat{GLu}_i$ 412, $\widehat{GLu}_o$ 422 and $\widehat{GLu}_m$ 432, as described below.

As shown in FIG. 4, a glucose insulin model 430 advantageously generates a continuous estimate of blood glucose $\widehat{GLu}_m$ 432 over time between the glucose spot checks 412, 422. Further, the glucose insulin model 430 advantageously generates continuous glucose estimates versus time, as described in detail with respect to FIGS. 5-11, below. The glucose insulin model 430 inputs user provided data including biographical data, such as age and weight, basal values (user initial conditions) and food and insulin intake data 403. Advantageously, optical data 424 derived from the optical sensor 402 is also utilized by the glucose insulin model 430 so as to detect physiological events, such as food intake and insulin injections, independent of user inputs 403.

Figure 5:
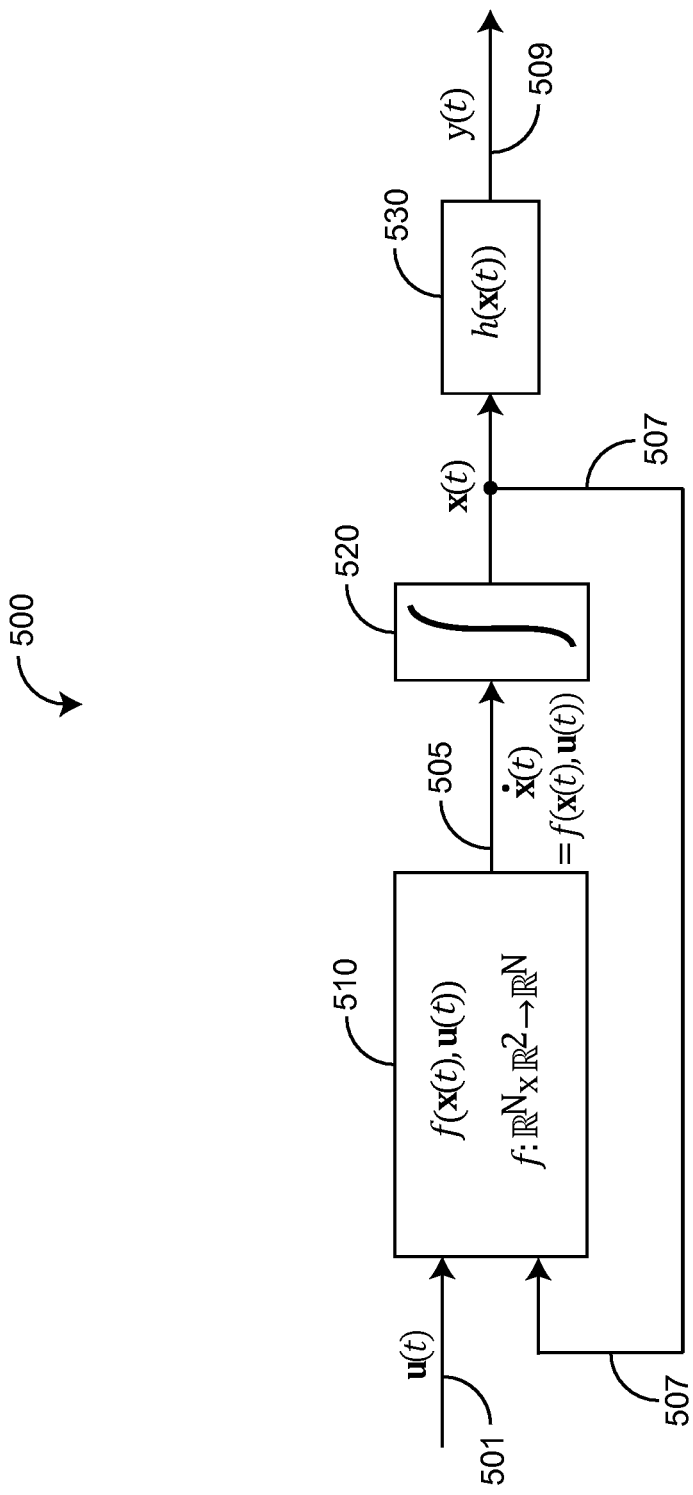
FIG. 5 is a general block diagram of a nonlinear state-space model governing glucose and insulin reactions in the human body.

FIG. 5 generally illustrates a nonlinear state-space model 500 that provides a modeled glucose output y(t) based upon glucose and insulin reactions in the human body. The state-space model 500 advantageously predicts blood glucose levels 509 based upon a subject's food and insulin intake 501. In particular, the state-space model 500 has a state equation block 510 that outputs the mathematical description 505 of the glucose and insulin reactions in the human body; a state vector block 520 that solves that mathematical description to generate state variables 507 and an output block 530 that generates a modeled blood glucose 509 output.

As shown in FIG. 5, in an embodiment, the state equation block 510 has an input vector u(t) 501 of insulin and food intake. The state equation block 510 generates an N-dimensional state equation $\dot{x}(t)$ 505 from the input vector u(t) 501 and a state vector x(t) 507. The state vector block 520 solves the state equation $\dot{x}(t)$ 505 to output the N-dimensional state vector x(t) 507. The output block 530 generates the modeled blood glucose y(t) 509 from the state vector x(t) 507. In an embodiment, the input vector u(t) 501 is a two-dimensional vector of insulin intake IIR(t) and glucose intake D(t) and the output y(t) 509 is a modeled blood glucose $\widehat{GLu}_m$, as described in detail with respect to FIGS. 10-11, below.

Figure 6A:
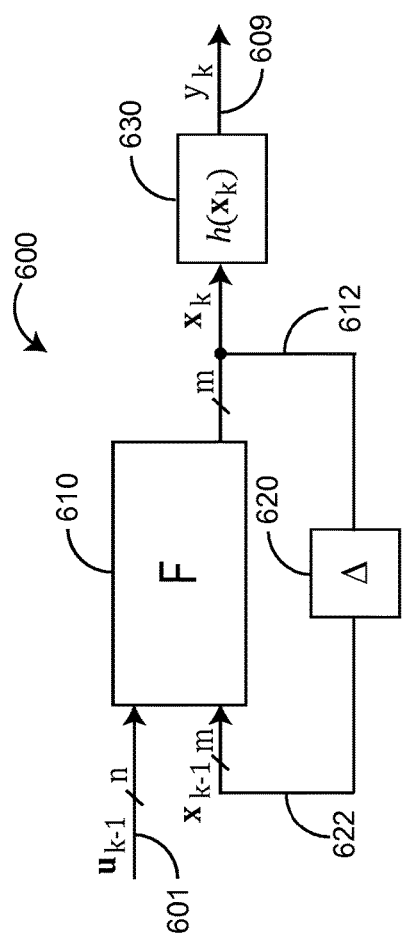
FIGS. 6A-B are a general block diagram of a discrete nonlinear state-space model governing glucose and insulin reactions in the human body and a graph of a corresponding glucose interval estimate.
Figure 6B:
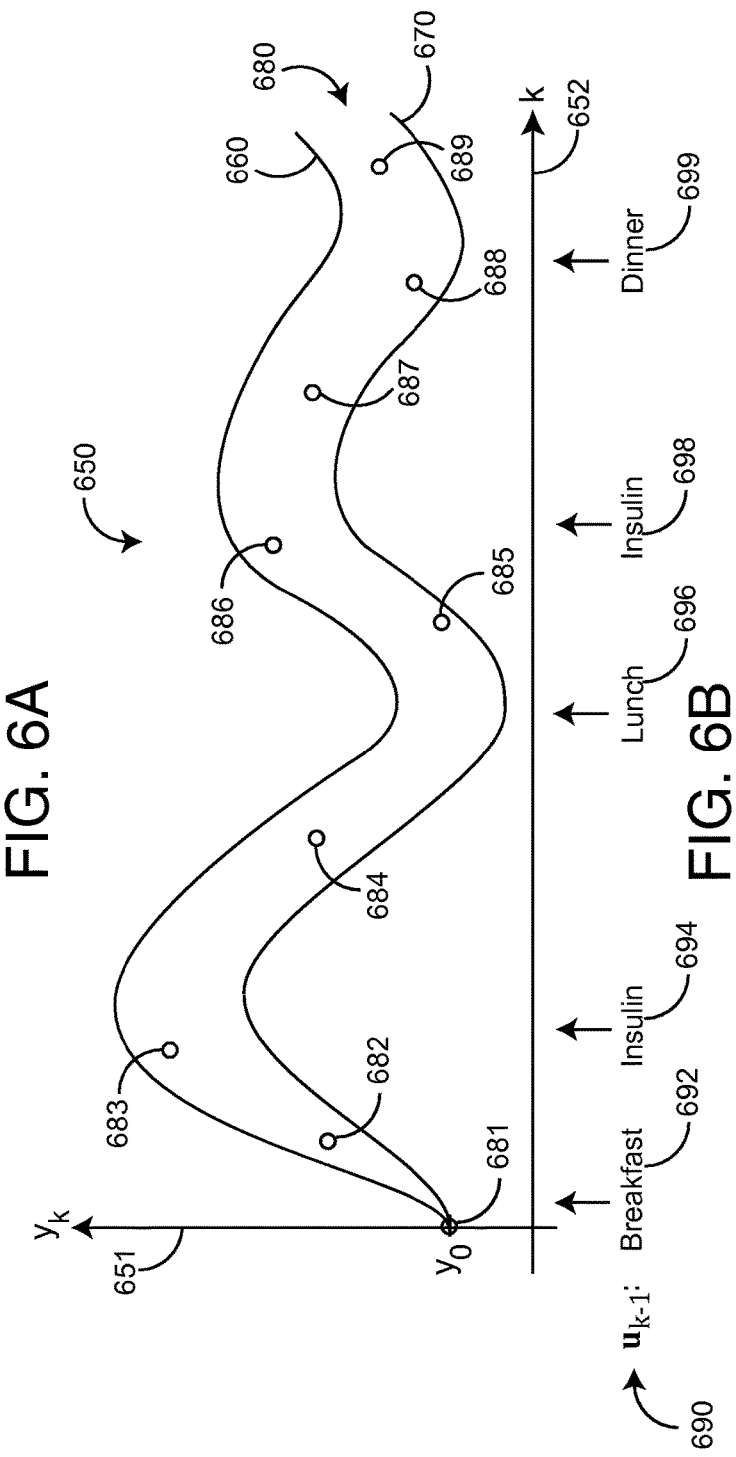

FIGS. 6A-B generally illustrate a discrete nonlinear state-space model 600 (FIG. 6A) and graphically illustrate corresponding interval estimates 650 (FIG. 6B) resulting from solutions to the state-space model differential equations. As shown in FIG. 6A, the discrete state-space model 600 has a state-space function block F 610 having an input vector $u_{k-1}$ 601 and a state vector $x_k$ 612 output. The state vector $x_k$ 612 is delayed one discrete time interval 620 to generate a delayed state vector $x_{k-1}$ 622 input to the function block F 610. An output block 630 inputs the state vector $x_k$ 612 and generates a modeled blood glucose level $y_k$ 609 output over discrete time k. State-space equations F 610 are a discrete time version of the state equation block 510 (FIG. 5) and state vector block 520 (FIG. 5) described above.

As shown in FIG. 6B, blood glucose interval estimates 650 derived from the state-space model 600 (FIG. 6A) are plotted on a blood glucose $y_k$ 651 axis versus a k (discrete time) axis 652. Numerical interval simulation (NIS) determines a glucose envelope 660, 670 for the glucose model state variable derivatives 612, which are described in further detail with respect to FIG. 10, below. In an embodiment, Runge-Kutta fourth order (RK4) NIS is used for calculating the envelope 660, 670.

The result are "fuzzy" blood glucose outputs $y_k$ 660, 670. The input vector $u_{k-1}$ 601 (FIG. 6A) includes food and insulin intakes 690. Also shown for reference are blood glucose spot checks 680, which can be invasive (test strip) or noninvasive (optical sensor).

Further shown in FIG. 6B are exemplar spot checks 680 and intakes 690. For example, the intervals 660, 670 each start from an initial blood glucose spot check, $y_0$ 681. Later in the day, breakfast is eaten 692. Sometime later, another spot check 682 is taken, showing a rise in blood glucose. A further spot check 683 at a later time reveals a relatively high blood glucose, prompting an insulin intake 694. Blood glucose drops 660, 670, as verified by an additional spot check 684.

Continuing with respect to FIG. 6B, lunch is eaten 696. A later spot check 685 shows a blood glucose rise, followed by a further spot check 686 showing a still higher blood glucose and prompting another insulin intake 698. A couple later spot checks 687, 688 show that blood glucose is decreasing in response. Dinner is eaten 699. The latest spot check 689 shows glucose rising once again. In an embodiment, blood glucose interval estimates 660, 670 are combined with the spot checks 680. For example, calculations of the interval estimates 660, 670 begin at a new initial condition for each spot check 680. In an embodiment, the new initial conditions are at the spot check value for invasive spot checks and are at an interval for noninvasive (less accurate) spot checks.

FIGS. 7A-B illustrate blood glucose interval estimates where the state-space model 600 (FIG. 6A) incorporates and is responsive to both invasive and noninvasive blood glucose spot checks. In an embodiment, blood glucose interval estimates 730, 740 are combined with the spot checks 790.

As shown in FIG. 7A, in an embodiment 701, calculations of the upper interval estimate 730 and lower interval estimate 740 begin at new (upper and lower) initial conditions for each spot check 790. In an embodiment, the interval for noninvasive (less accurate) spot checks 750 is larger than the interval for invasive (more accurate) spot checks 760. The result is a revised upper estimate 770 and revised lower estimate 780. In general, the interval between revised upper and lower estimates 770, 780 is less (more accurate) in view of the increased accuracy of the glucose-insulin model in view of the optical and invasive spot check measurements.

As shown in FIG. 7B, in an embodiment 702, the noninvasive spot checks 750 provide a spot check interval and the invasive spot checks 760 provide a spot check point. The result is a revised upper estimate 770 and revised lower estimate 780 for noninvasive spot checks 750 and a revised point estimate 760 for invasive spot checks.

Figure 8:
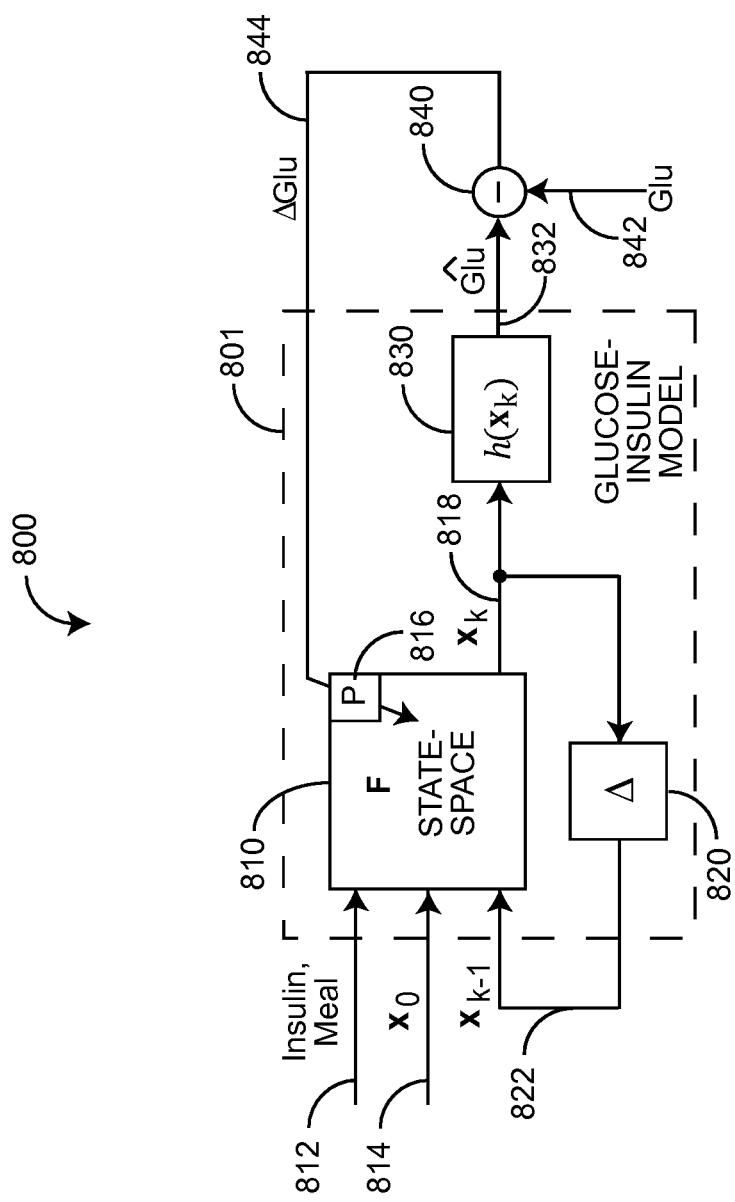
FIG. 8 is a block diagram of dynamic optimization of a blood glucose-insulin model that inputs insulin and meal intake data and outputs modeled blood glucose values.

FIG. 8 generally illustrates a dynamic optimizer 800 for a glucose-insulin model 801. The glucose-insulin model 801 has a state-space function (F) block 810, a delay block 820 and an output function block 830, as described with respect to FIGS. 6A-B, above. The glucose-insulin model 801 has insulin and meal 812 and state variable initialization $x_0$ 814 inputs and generates an a blood glucose model $\widehat{GLu}$ 832 output. The glucose-insulin model 801 is described generally with respect to FIGS. 4-5, above, and a glucose-insulin model embodiment is described in detail with respect to Appendix A, attached hereto.

As shown in FIG. 8, the state-space function block F 810 generates a $x_k$ 818 state variable output based upon a predetermined set of parameters P 816. State variable $x_k$ 818 is delayed to generate a delayed state variable $x_{k-1}$ 822 input. The output function $h(x_k)$ block 830 generates the blood glucose model output $\widehat{GLu}$ 832. Dynamic optimization repeatedly calculates a difference 840 of measured blood glucose Glu 842 and calculated blood glucose $\widehat{GLu}$ 832 so as to generate ΔGlu 844. The parameters P 816 are recursively adjusted so as to minimize ΔGlu 844. The resulting optimized parameters are then locked into the state-space function block F 810.

Figure 9:
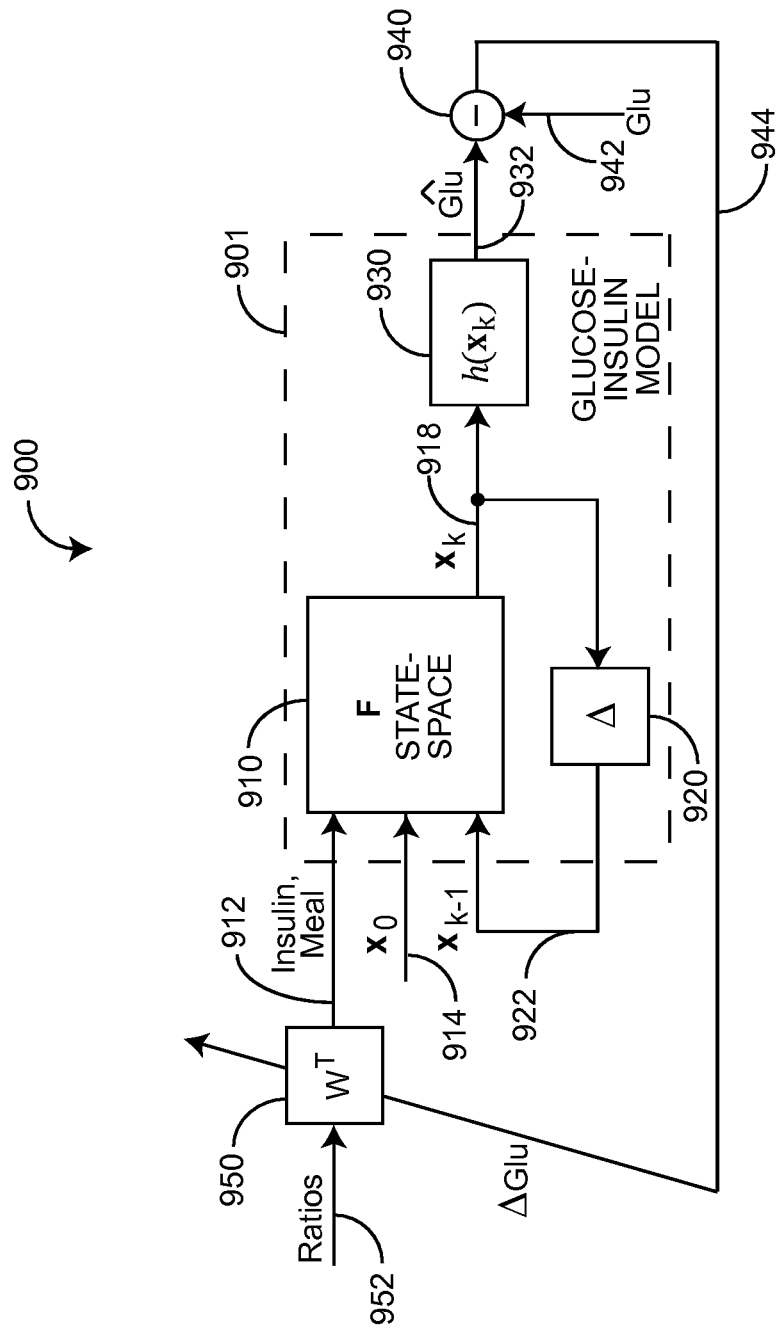
FIG. 9 is a block diagram of dynamic optimization of a blood glucose-insulin model having optical-sensor-generated light absorption ratio inputs for estimating insulin and meal intakes.

FIG. 9 generally illustrates an alternative dynamic optimizer 900 for a glucose-insulin model 901 that utilizes optical-sensor-derived light absorption ratios 952 in lieu of insulin and meal inputs 812 (FIG. 8). The glucose-insulin model 901 has a state-space functions (F) block 910, a delay block 920 and an output function block 930, as described with respect to FIG. 8, above. The glucose-insulin model 901 has estimated insulin and meal 912 inputs and state variable initialization $x_0$ 914 inputs and generates an a blood glucose model output $\widehat{GLu}$ 932. The glucose-insulin model 901 is described generally with respect to FIG. 8, above, and a glucose-insulin model embodiment is described in detail with respect to FIG. 10, below.

As shown in FIG. 9, insulin and meal 912 inputs are estimated by a weighted sum of optic sensor-derived ratios 952, where the where the weights are dynamically optimized to minimize the difference ΔGlu 944 between the model-derived glucose output $\widehat{GLu}$ 932 and measured blood glucose Glu 942. The resulting optimized weights 950 are then "locked-in" for estimating the insulin, meal inputs 912.

Figure 10:
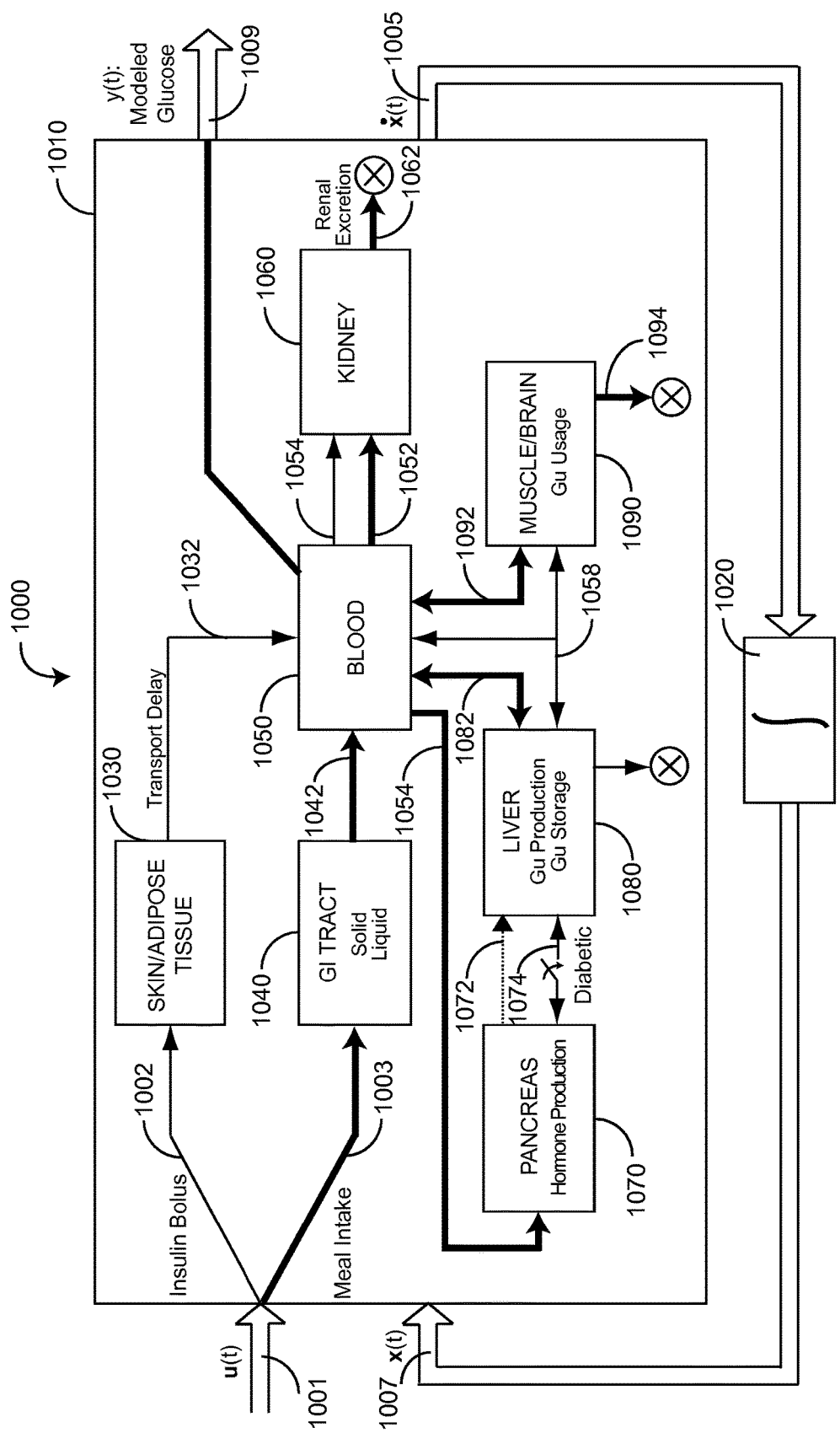
FIG. 10 is a detailed block diagram of a nonlinear state space model for glucose and insulin reactions in the human body.

FIG. 10 illustrates a nonlinear state space model 1000 governing glucose and insulin reactions in the human body. The model advantageously predicts blood glucose levels 1009 based upon a subject's food and insulin intake 1001. In particular, the state space model 1000 has a state equation block 1010 that outputs the mathematical description 1005 of the glucose and insulin reactions in the human body; a state vector block 1020 that solves that mathematical description to generate state variables 1007 and an output block 1030 that generates a modeled blood glucose output 1009.

As shown in FIG. 10, in an embodiment, the state equation block 1010 has an input vector u(t) 1001 of insulin and food intake. The state equation block 1010 generates an N-dimensional state equation ẋ(t) 1005 from the input vector u(t) 1001 and a state vector x(t) 1007. The state vector block 1020 solves the state equation ẋ(t) 1005 to output the N-dimensional state vector x(t) 1007. The output block 1030 generates a modeled blood glucose y(t) output 1009 from the state vector x(t) 1007. In an embodiment, the input vector u(t) 1001 is a two-dimensional vector of insulin intake IIR(t) and glucose intake D(t) and the output y(t) 1009 is a blood glucose level G(t). Table I summarizes this glucose predictor model.

TABLE 1

| | |
|---|---|
| Inputs (u ∈ $\mathbb{R}^2$) | Insulin intake IIR(t) and glucose intake D(t). |
| Parameters: | Patient body weight (kg), basal insulin $I_b$ (pmol/L) if insulin is secreted and basal exogenous insulin infusion rate $IIR_b$ (pmol/kg) if insulin is injected, basal blood glucose level $G_b$, and basal endogenous glucose production $EGP_b$. |
| Output (y ∈ $\mathbb{R}$) | Blood glucose level G(t). |

Also shown in FIG. 10, the state space model 1000 has a state equation block 1010 and a state vector block 1020. An input u(t) 1001 to the state equation block 1010 describes insulin bolus 1002 and meal 1003 intakes and models various body functions. The state equation block 1010 models the response of various body organs and fluids to the insulin 1002 and meal 1003 intakes. The state vector block 1020 solves the state equation block 1010 to generate the state x(t) 1007, which is also input to the state equation block 1010. In response to the input u(t) and state x(t), the state equation block 1010 generates an output y(t) 1009 of modeled blood glucose.

As shown in FIG. 10, the physiological compartments in the model 1000 include skin and adipose (fat) tissue 1030, the GI tract 1040, blood 1050, kidneys 1060, the pancreas 1070, the liver 1080 and the brain and muscles 1090. A meal intake 1003 is digested in the GI tract 1040, which transports glucose 1042 to the blood stream 1050, which provides a modeled blood glucose y(t) 1009 output. The kidneys 1060 filter out some blood glucose 1052, which is excreted 1062. The pancreas 1070 converts some blood glucose 1054 to glucagon 1072, which is stored in the liver 1080. The liver 1080 also regulates blood glucose 1082 via glucose production to and storage from the blood stream 1050. The muscles and brain 1090 use a substantial quantity 1094 of blood glucose, exchanging blood glucose 1092 with the blood stream 1050 in the process.

Further shown in FIG. 10, insulin 1002 is injected into the skin/adipose tissue 1030, which enters the blood stream 1050 after a transport delay 1032. The kidneys 1060 filter out some insulin 1054, which is excreted 1062. The blood stream 1050 exchanges insulin 1058 with the liver 1080 and muscle/brain 1090. In a diabetic 1074, insulin 1074 is exchanged between the pancreas 1070 and liver 1080.

The state equation ẋ(t) is slightly different between types of subjects, i.e. those who are normal, those who have type I diabetes and those who have type II diabetes. In particular, ẋ(t) distinguishes subjects who secrete insulin and inject insulin, as shown in Table 2, below.

TABLE 2

| | Insulin Secreted | Insulin Injected |
|---|---|---|
| Normal | Yes | No |
| Type I | No | Yes |
| Type II | Yes | Yes |

EQS. 1-2 are the state variable x(t) and state equation ẋ(t) according to FIG. 10, described above. Table 3, below describes the individual elements of the state variable x(t).

$$x(t) = \begin{bmatrix} Y(t) \\ G_{plasma}(t) \\ G_{tissue}(t) \\ X(t) \\ I_{liver}(t) \\ I_{plasma}(t) \\ I_{portal}(t) \\ I_1(t) \\ I_d(t) \\ Q_{solid}(t) \\ Q_{liquid}(t) \\ Q_{gut}(t) \\ I_{poly1}(t) \\ I_{mono1}(t) \\ \vdots \\ I_{polyN}(t) \\ I_{monoN}(t) \\ GL(t) \\ GLY(t) \\ A_{GL}(t) \end{bmatrix} \quad \text{EQ. 1}$$

$$\begin{bmatrix} \dot{x}(t) \end{bmatrix} = \begin{bmatrix} -\alpha\left(Y(t) - \max\left(-S_b, \beta\left(\dfrac{G_{plasma}(t)}{V_G} - h\right)\right)\right) \\ EGP(t) - GLY_r + Ra(t) - U_{ii}(t) - E(t) - k_1 G_{plasma}(t) + k_2 G_{tissue}(t) \\ -U_{id}(t) + k_1 G_{plasma}(t) - k_2 G_{tissue}(t) \\ -p_{2U}X(t) + p_{2U}\left(\dfrac{I_{plasma}(t)}{V_1} - I_b\right) \\ -(m_1 + m_3(t))I_{liver}(t) + m_2 I_{plasma}(t) + \gamma I_{portal}(t) \\ -(m_2 + m_4)I_{plasma}(t) + m_1 I_{liver}(t) + R_i(t) \\ -\gamma I_{portal}(t) + Y(t) + S_b + \max\left(0, K\dfrac{G_{plasma}(t)}{V_G}\right) \\ -k_i I_1(t) + \dfrac{k_i}{V_I} I_{plasma}(t) \\ k_i I_1(t) - k_i I_d(t) \\ -k_{grind}Q_{solid}(t) + D(t) \\ k_{grind} \cdot Q_{solid}(t) - k_{empty}(t) \cdot Q_{liquid}(t) \\ k_{empty}(t) \cdot Q_{liquid}(t) - k_{absorb} \cdot Q_{gut}(t) \\ -(k_d + k_{a1})I_{poly[brand1]}(t) + IIR_{brand1}(t) \\ k_d I_{poly[brand1]}(t) - k_{a2}I_{mono[brand1]}(t) \\ \vdots \\ -(k_d + k_{a1})I_{poly[brandN]}(t) + IRR_{[brandN]}(t)(t) \\ k_d I_{poly[brandN]}(t) - k_{a2}I_{mono[brandN]}(t) \\ -k_{GL}GL + GL_b\left(\dfrac{t_{INS}}{t_{INS} + \dfrac{I_L}{V_I}}\right) + GL_{b,r}\left(\dfrac{1}{1 + \left(\dfrac{G}{t_G}\right)^{\eta_G}}\right) * \\ \left(\dfrac{1}{1 + \left(\dfrac{GL(t - t_{delay})}{t_{GL}}\right)^{\eta_{GL}}}\right) * \left(\dfrac{t_{INS}}{t_{INS} + \dfrac{I_L}{V_I}}\right) \\ (GLY_r - GLY_d)\text{body weight} \\ k_{GL_A}\left(\dfrac{\tanh fun\left(GL_M, \dfrac{GL}{GL_b}\right) - 1}{2} - A_{GL}\right) \end{bmatrix} \quad \text{EQ. 2}$$

TABLE 3

| State Variable | Meaning | Dimensions |
|---|---|---|
| Y | Insulin Secretion Rate | pmol/(kg*min) |
| $G_{plasma}$ | Plasma Glucose | mg/kg |
| $G_{tissue}$ | Tissue Glucose | mg/kg |
| X | Insulin in interstitial fluid | pmol/L |
| $I_{liver}$ | Insulin in liver | pmol/kg |
| $I_{plasma}$ | Insulin in plasma | pmol/kg |
| $I_{portal}$ | Insulin in portal vein | pmol/kg |
| $I_1$ | | pmol/L |
| $I_d$ | Delayed insulin signal | pmol/L |
| $Q_{solid}$ | Glucose in stomach at solid phase | mg |
| $Q_{liquid}$ | Glucose in stomach at liquid phase | mg |
| $Q_{gut}$ | Glucose in intestine | mg |
| $I_{poly}$ | Non-monomeric insulin in subcutaneous space | pmol/kg |

TABLE 3-continued

| State Variable | Meaning | Dimensions |
|---|---|---|
| $I_{mono}$ | Monomeric insulin in subcutaneous space | pmol/kg |
| GL | Glucagon hormone | pg/ml |
| GLY | Pro-glycogen | mg |
| $A_{GL}$ | Glucagon rate affected endogenous glucose factor | [ ] |

GL accounts for diabetic I complications while satisfying normal patients in the glucagon system. GL is used in $A_{GL}$. GLY has two separate paths to the liver. With the exception of Y and $A_{GL}$, which are rates instead of physical quantities, all state variables must be non-negative. All basal quantities are marked by a subscript 'b' and are not time dependent.

Table 4, below, provides model parameters for the normal and the type 2 diabetic subject. Table 5, below, provides parameters of subcutaneous insulin kinetics, glucose sensor delay and PID controller. Table 6, below, provides additional constants.

TABLE 4

| Process | Parameter | Normal Value | Type 2 Diabetic Value | Unit |
|---|---|---|---|---|
| Glucose Kinetics | $V_G$ | 1.88 | 1.49 | dl/kg |
| | $k_1$ | 0.065 | 0.042 | min$^{-1}$ |
| | $k_2$ | 0.079 | 0.071 | min$^{-1}$ |
| Insulin Kinetics | $V_i$ | 0.05 | 0.04 | l/kg |
| | $m_1$ | 0.190 | 0.379 | min$^{-1}$ |
| | $m_2$ | 0.484 | 0.673 | min$^{-1}$ |
| | $m_4$ | 0.194 | 0.269 | min$^{-1}$ |
| | $m_5$ | 0.0364 | 0.0526 | min kg/pmol |
| | $m_6$ | 0.6471 | 0.8118 | dimensionless |
| | HE | 0.6 | 0.6 | dimensionless |
| Rate of Appearance | $k_{max}$ | 0.0558 | 0.0465 | min$^{-1}$ |
| | $k_{min}$ | 0.0080 | 0.0076 | min$^{-1}$ |
| | $K_{abl}$ | 0.057 | 0.023 | min$^{-1}$ |
| | k | 0.558 | 0.0465 | min$^{-1}$ |
| | f | 0.90 | 0.90 | dimensionless |
| | α | 0.00013 | 0.00006 | mg$^{-1}$ |
| | b | 0.82 | 0.68 | dimensionless |
| | c | 0.00236 | 0.00023 | mg$^{-1}$ |
| | d | 0.010 | 0.09 | dimensionless |
| Endogenous Production | $k_{g1}$ | 2.70 | 3.09 | mg/kg/min |
| | $k_{g2}$ | 0.0021 | 0.0007 | min$^{-1}$ |
| | $k_{g3}$ | 0.009 | 0.005 | mg/kg/min per pmol/l |
| | $k_{g1}$ | 0.0618 | 0.0786 | mg/kg/min per pmol/kg |
| | $k_1$ | 0.0079 | 0.0066 | min$^{-1}$ |
| Utilization | F | 1 | 1 | mg/kg/min |
| | V | 2.50 | 4.65 | mg/kg/min |
| | V | 0.047 | 0.034 | mg/kg/min per pmol/l |
| | K | 225.59 | 466.21 | mg/kg |
| | P | 0.0331 | 0.0840 | min$^{-1}$ |
| Secretion | K | 2.30 | 0.99 | pmol/kg per (mg/dl) |
| | α | 0.050 | 0.013 | min$^{-1}$ |
| | β | 0.11 | 0.05 | pmol/kg/min per (mg/dl) |
| | γ | 0.5 | 0.5 | min$^{-1}$ |
| Renal Excretion | $k_{c1}$ | 0.0005 | 0.0007 | min$^{-1}$ |
| | $k_{c2}$ | 339 | 269 | mg/kg |

TABLE 5

| Control | Parameter | Value | Unit |
|---|---|---|---|
| Subcutaneous insulin kinetics | $k_a$ | 0.0164 | min$^{-1}$ |
| | $k_{a1}$ | 0.0018 | min$^{-1}$ |
| | $k_{a2}$ | 0.0182 | min$^{-1}$ |
| Glucose sensor delay | $T_a$ | 10 | pmol/kg/min per mg/dl |
| PID controller | $K_p$ | 0.032 | min |
| | $T_Q$ | 66 | min |
| | $T_I$ | 450 | min |

TABLE 6

Figure 11:
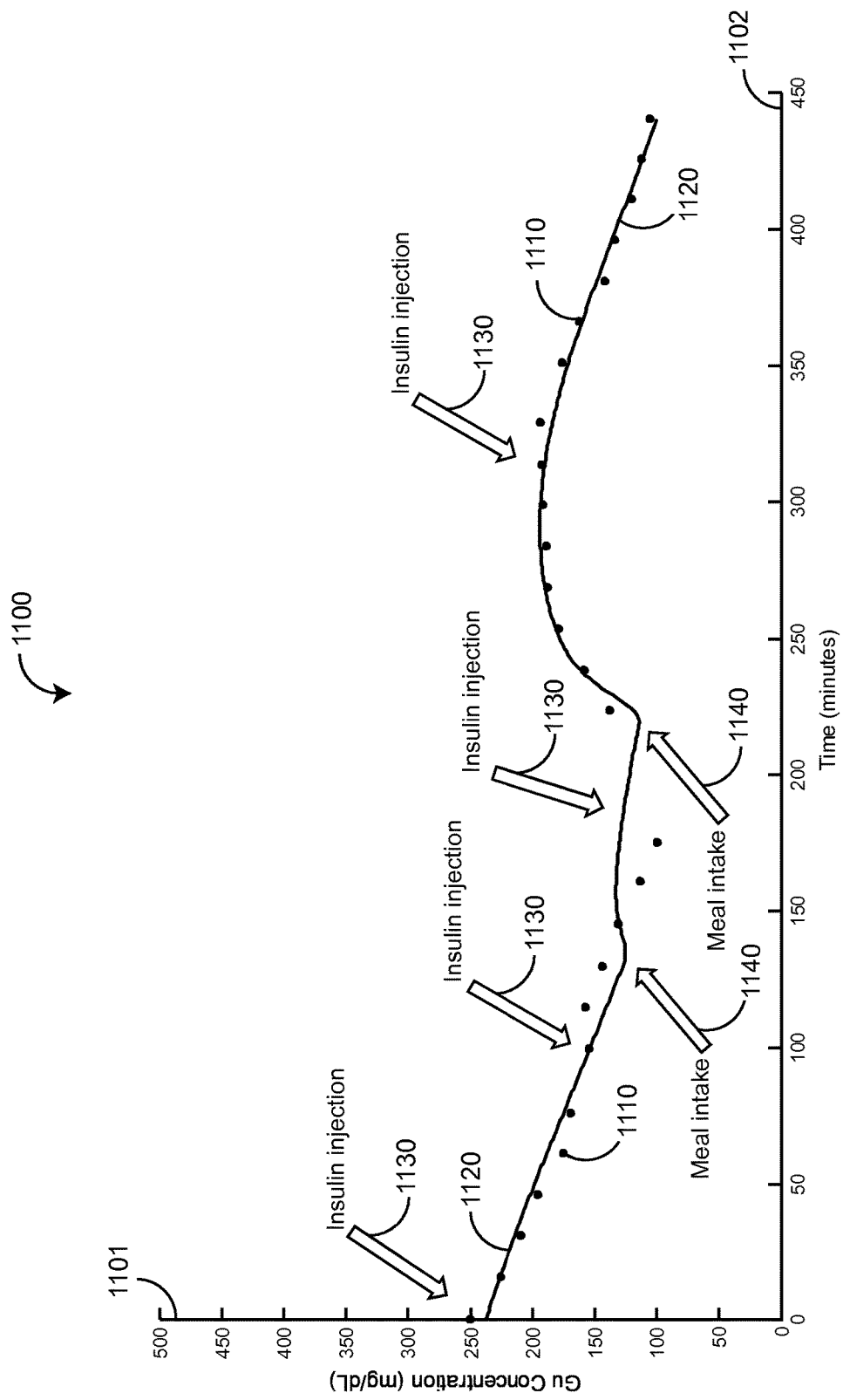
FIG. 11 is a blood glucose versus time graph comparing glucose model predictions to blood glucose measurements.

$f_{GLY} = 0.25$
$GLY_{synth} = [0.2025927654630183 \ 0.1865908261637011 \ 0.0370319118341182 - 164.7045696728318700]$
$k_{1_A} = 1/25$
$I_A = [1.21 - 1.14 \ 1.66 - 0.88]$
$G_M = [1.425 - 1.406 \ 0.619 - 0.49]$
$K_{GL_A} = 1/65$
$G_{L_M} = [0.7 \ 0.37 - 36]$
$f_{GNG \ resting} = 0.25$
$GLY_{max} = 90000$
$t_{delay} = 3$
$GLY_{soft} = [0 \ 1 - 1/1000 - GLY_{max}]$ FIG. 11 is a blood glucose 1101 versus time 1102 graph 1100 comparing glucose model predictions 1120 (line) to invasive blood glucose measurements 1110 (dots). The graph also illustrates the impact of insulin injections 1130 and meal intakes 1140.

A glucose estimator has been disclosed in detail in connection with various embodiments. These embodiments are disclosed by way of examples only and are not to limit the scope of the claims herein. One of ordinary skill in art will appreciate many variations and modifications.

What is claimed is:

1. A blood glucose sensing system comprising:
a plurality of physiological sensors configured to provide sensor data associated with a user, the plurality of physiological sensors comprising an invasive sensor and an optical blood glucose sensor configured to generate blood glucose data of a user;
an input for receiving a plurality of blood glucose values derived from the invasive sensor data;
one or more hardware signal processors configured to:
receive blood glucose data from the optical blood glucose sensor;
receive a plurality of user-specific data, the user-specific data comprising food intake data and insulin intake data;
detect physiological events to generate a plurality of physiological event data based at least in part on the optical sensor data and independent of user input;
determine, using a glucose insulin estimator, a plurality of modeled blood glucose values over time between measurements by the blood glucose sensor, wherein the plurality of modeled blood glucose values are determined based on the blood glucose data and user-specific data, wherein the glucose insulin estimator comprises a nonlinear state-space model of glucose and insulin reactions within a human body and state variables associated with at least one of insulin secretion rate, plasma glucose, tissue glucose, insulin in interstitial fluid, insulin in liver, insulin in plasma, insulin in portal veins, delayed insulin signal, glucose in the stomach at solid phase, glucose in the stomach at liquid phase, glucose in the intestine, non-monomeric insulin in the subcutaneous space, monomeric insulin in the subcutaneous space, glucagon hormone, pro-glycogen, or glucagon rate affected endogenous factor, or parameters associated with at least one of glucose kinetics, insulin kinetics, rate of appearance of insulin, endogenous production of insulin, utilization of insulin, secretion of insulin, or renal excretion of insulin; and dynamically optimize the nonlinear state-space model to minimize an error between the plurality of modeled blood glucose values of the user and measured values of blood glucose, wherein the measured values of blood glucose comprise blood glucose values derived from the invasive sensor data and blood glucose values derived from the optical sensor data, wherein an input of the state-space model comprises the plurality of physiological event data of the user; and determine a continuous estimate of blood glucose over a period of monitoring time based on a combination of the plurality of blood glucose values and the plurality of modeled blood glucose values; and a display configured to display a glucose trend over time, the glucose trend based at least in part on the plurality of modeled blood glucose values.

2. The blood glucose sensing system of claim 1, wherein the user-specific data further comprises one or more of biographical data and basal values.

3. The blood glucose sensing system of claim 1, wherein user-specific data is manually inputted.

4. The blood glucose sensing system of claim 1,
wherein the one or more hardware signal processors are configured to generate a blood glucose estimate based at least in part on each of the plurality of modeled blood glucose values, a plurality of noninvasive sensor data and a plurality of invasive sensor data, and wherein the one or more hardware signal processors are configured to recursively adjust parameters of the state-space model to minimize an error between the plurality of modeled blood glucose values of the user and measured values of blood glucose, the blood glucose estimate based at least in part on the state-space model having parameters resulting in minimal error between the plurality of modeled blood glucose values of the user and measured values of blood glucose.

5. The blood glucose sensing system of claim 4, the one or more hardware processors configured to determine a continuous blood glucose estimate over a period of monitoring time.

6. The blood glucose sensing system of claim 4, wherein the state-space model comprises:
an input vector comprising an insulin intake and food intake;
a state vector comprising the state variables;
a state equation comprising the parameters; and
the modeled blood glucose values.

7. The blood glucose sensing system of claim 6, wherein the state equation comprises state variables associated with insulin secretion rate, plasma glucose, tissue glucose, insulin in interstitial fluid, insulin in liver, insulin in plasma, insulin in portal vein, delayed insulin signal, glucose in stomach at solid phase, glucose in stomach at liquid phase, glucose in intestine, non-monomeric insulin in subcutaneous space, monomeric insulin in subcutaneous space, glucagon hormone, pro-glycogen, and glucagon rate affected endogenous factor.

8. The blood glucose sensing system of claim 1, wherein the one or more hardware signal processors is configured to detect physiological events to generate a plurality of physiological event data based at least in part on the sensor data and independent of user input.

9. A method for blood glucose monitoring, the method comprising:
generating, using an invasive blood glucose sensor and an optical blood glucose sensor, blood glucose data of a user;
receiving, using one or more hardware processors, the blood glucose data;
receiving, using the one or more hardware processors, a plurality of user-specific data, the user-specific data comprising food intake data and insulin intake data;
determining, using the one or more hardware processors implementing a glucose insulin model, a plurality of modeled blood glucose values over time between measurements by the blood glucose sensor, wherein the plurality of modeled blood glucose values are determined based on the blood glucose data and user-specific data, wherein the glucose insulin model is a nonlinear state-space model of glucose and insulin reactions within a human body, and wherein the glucose insulin model comprises:
state variables associated with at least one of insulin secretion rate, plasma glucose, tissue glucose, insulin in interstitial fluid, insulin in liver, insulin in plasma, insulin in portal vein, delayed insulin signal, glucose in stomach at solid phase, glucose in stomach at liquid phase, glucose in intestine, non-monomeric insulin in subcutaneous space, monomeric insulin in subcutaneous space, glucagon hormone, pro-glycogen, or glucagon rate affected endogenous factor, or
parameters associated with at least one of glucose kinetics, insulin kinetics, rate of appearance of insulin, endogenous production of insulin, utilization of insulin, secretion of insulin, or renal excretion of insulin;
dynamically optimizing the glucose insulin model to minimize an error between the plurality of modeled blood glucose values of the user and measured values of blood glucose based on the blood glucose data of the user; and
displaying a glucose trend over time, the glucose trend based at least in part on the plurality of modeled blood glucose values.

10. The method of claim 9, wherein the user-specific data comprises one or more of biographical data and basal values.

11. The method of claim 9, comprising inputting a plurality of user-specific data.

12. The method of claim 9, comprising:
generating, using the one or more hardware processors, a blood glucose estimate based at least in part on each of the plurality of modeled blood glucose values, a plurality of noninvasive sensor data and a plurality of invasive sensor data,
wherein, using the one or more hardware processors, the blood glucose estimate is generated at least in part by recursively adjusting parameters of a state-space model to minimize an error between the plurality of modeled blood glucose values of the user and measured values of blood glucose.

13. The method of claim 12, generating the blood glucose estimate comprising generating a continuous blood glucose estimate over a period of monitoring time.

14. The method of claim 12, wherein the nonlinear state-space model comprises:

an input vector comprising an insulin intake and food intake;
a state vector comprising the state variables;
a state equation comprising the parameters; and
the modeled blood glucose values.

15. The method of claim 14, wherein the nonlinear state-space model comprises state variables associated with insulin secretion rate, plasma glucose, tissue glucose, insulin in interstitial fluid, insulin in liver, insulin in plasma, insulin in portal vein, delayed insulin signal, glucose in stomach at solid phase, glucose in stomach at liquid phase, glucose in intestine, non-monomeric insulin in subcutaneous space, monomeric insulin in subcutaneous space, glucagon hormone, pro-glycogen, and glucagon rate affected endogenous factor.

16. The method of claim 9, wherein the blood glucose sensor is a non-invasive blood glucose sensor.

17. The method of claim 16, wherein the non-invasive blood glucose sensor is an optical sensor.

18. The method of claim 9, comprising detecting physiological events to generate a plurality of physiological event data based at least in part on the sensor data and independent of user input.

* * * * *